United States Patent [19]
Brandt et al.

[11] Patent Number: 5,610,280
[45] Date of Patent: Mar. 11, 1997

[54] MONOCLONAL ANTIBODIES AGAINST MELANOMA

[75] Inventors: Michael Brandt, Iffeldorf; Josef Endl, Weilheim; Herbert Jungfer, Starnberg; Winfried Albert, Eberfing, all of Germany

[73] Assignee: Boehringer Mannheim GmbH, Mannheim-Waldhof, Germany

[21] Appl. No.: 214,020

[22] Filed: Mar. 15, 1994

Related U.S. Application Data

[63] Continuation of Ser. No. 773,796, Oct. 9, 1991, abandoned.

[30] Foreign Application Priority Data

Oct. 11, 1990 [DE] Germany ............... 40 32 312.9
Mar. 6, 1991 [DE] Germany ............... 41 07 154.9

[51] Int. Cl.$^6$ ............... A61K 51/10; C07K 16/00; G01N 33/53; C12N 5/12
[52] U.S. Cl. ............... 530/387.5; 530/388.8; 530/391.3; 435/70.21; 435/172.2
[58] Field of Search ............... 530/307.5, 391.3, 530/388.8; 435/70.21, 172.2, 240.27

[56] References Cited

U.S. PATENT DOCUMENTS 4,816,567  3/1989  Cabilly et al. ............... 530/387

FOREIGN PATENT DOCUMENTS 0280209  8/1988  European Pat. Off. .
0316882  5/1989  European Pat. Off. .

OTHER PUBLICATIONS

Roitt *Immunology* p. 18.11 1985.
Queen et al PNAS 86:10029–10033 1989.
Sonnino et al *In: The Molecular Immunology of Complex Carbohydrates* Ed Am Wo & LG Adams Plenum Press NY pp. 437–464 '88.
Paul *Fundamental Immunology* pp. 35–36.
Hellstrom et al *Monoclonal Antibodies for Cancer Detection & Therapy* Chapter 2 1985.
Portoukalian, et al BBRC 85: 916–920 '78.
Yamaguchi, et. al PNAS 84: 2416–2420 '87.
Jonak, et. al Adv Drug Delivery Reviews 2:207–228 '88.
"Regression of cutaneous metastatic melanoma by intralesional injection with human monoclonal antibody to ganglioside GD2", by Reiko F. Irie and Donald L. Morton, *Proc. Nat'l Acad. Sci. USA*, vol. 83, pp. 8694–8698, Nov. 1986, Immunology.
"Human–Human Monoclonal Antibody Directed Against Tumor Surface Antigen in the Treatment of Human Malignancy", by Kenneth Alonso, M.D., F.A.C.P., *American Journal of Clinical Oncology (CCT)*.
"Human Monoclonal Antibody to Ganglioside GM2 for Melanoma Treatment", by Reiko F. Irie, Takasumi Matsuki & Donald L. Morton, *The Lancet*, Apr. 8, 1991.
"Remission Induction in Non–Hodgkin Lymphoma with Reshaped Human Monoclonal Antibody Campath–1H" *The Lancet*, Dec. 17, 1988.
Ravindranath et al., "Gangliosides as antigens of human melanoma", *Malignant Melanoma*, 1988 Kluwer Academic Publishers, Boston, p. 20.
Basu et al, "Expression of Glycosphingolipid Glycosyltransferases in Development and Transformation", *The Glycoconugates*, vol. III, pp. 265–281.
*Biochemistry*, 2nd Ed., Stanford University, 1975, pp. 462–463.
Carubia et al, "Gangliosides of Normal and Neoplastic Human Melanocytes", *Biochemical and Biophysical Research Communications*, vol. 120, No. 2, 1984, Apr. 30, 1984, pp. 500–504.
Tai et al, "Immunogenicity of Melanoma–Associated Gangliosides in Cancer Patients", *Int. J. Cancer*, 35, 607–612 (1985).
Furukawa et al, "Two Human Monoclongal Antibodies Reacting with the Major Gangliosides of Human Melanomas and Comparison with Corresponding Mouse Monoclonal Antibodies", *Cancer Research*, 49, 191–196, Jan. 1, 1989.
Furukawa et al, "Analysis of the Expression of N–Glycolylneuraminic Acid–containing Gangliosides in Cells and Tissues using Two Human Monoclonal Antibodies", *The Journal of Biological Chemistry*, vol. 263, No. 34 Dec. 4, 1988 pp. 18507–18512.
Singhai et al, "Molecular Changes in Carbohydrate Antigens Associated with Cancer", *BioEssays*, vol. 12, No. 5, May 1990, pp. 223–230.
Houghton et al, "Mouse monoclonal IgG3 antibody detecting $G_{D3}$ ganglioside: A phase I trial in patients with malignant melanoma", *Proc. Natl. Acad. Sci. USA*, vol. 82, pp. 1242–1246, Feb. 1985.
Irie et al., "Regression of cutaneous metastatic melanoma by intralesional injection with human monoclonal antibody to ganglioside GD2", *Proc. Natl. Acad. Sci. USA*, vol. 83, pp. 8694–8698, Nov. 1986.

*Primary Examiner*—Donald E. Adams
*Attorney, Agent, or Firm*—Nikaido Marmelstein Murray & Oram LLP

[57] ABSTRACT

The present invention provides a human monoclonal antibody against melanoma, characterized in that it binds to the gangliosides GM3 and GD3 but essentially does not bind to the gangliosides GM1, GM2, GD1a, GD1b and GD2, the binding of the antibody to the gangliosides having been determined by immune staining after thin layer chromatographic separation of the gangliosides. The present invention also provides a process for the production of human monoclonal antibodies directed against melanoma, wherein, without previous immunization, B-lymphocytes are isolated from a healthy person, the isolated B-lymphocytes are immortalized, antibodies from the immortalized B-lymphocytes are screened by immune-histochemical analysis for binding against melanoma and/or melanoma metastases, the positively reacting B-lymphocytes are selected, cultured and monoclonal antibodies obtained therefrom.

8 Claims, No Drawings

MONOCLONAL ANTIBODIES AGAINST MELANOMA

This application is a continuation of application Ser. No. 07/773,796 filed Oct. 9, 1991 now abandoned.

The present invention is concerned with a process for obtaining human antibodies which are directed against melanoma, with the antibodies obtained by the process according to the present invention and with the use thereof.

Melanoma, a tumour of the skin, is an extremely aggressive tumour. Especially metastasing melanoma can scarcely any longer be successfully treated by conventional methods. Therefore, there is a great need to find new therapeutics which can be used for the treatment of melanomas.

Dippold et al., (Proc. Natl. Acad. Sci. USA, 77, 6114–6118/1980) have reported the production of murine monoclonal antibodies against melanoma. One of the antibodies disclosed therein is directed against the ganglioside GD3. In J. Biol. Chem., 262, 6802–6807/1987 are also described murine monoclonal antibodies against melanoma. These bind equally to GM3 and GM2 but not to GD3.

In 1982, Irie et al. (Proc. Natl. Acad. Sci. USA, 79, 5666–5670/1982) reported the production of human monoclonal antibodies which react with melanoma. The monoclonal antibodies there disclosed react with the gangliosides GM2 and GD2, respectively. In Proc. Natl. Acad. Sci. USA, 84, 2416–2420/1987, are also described human monoclonal antibodies against melanoma. These bind strongly to GD3 and GD2 or to GM3 and GD1a, respectively. In Cancer Research, 49, 191–196/1989, are also described human monoclonal antibodies against melanoma. These bind strongly to GM3 and GD1a or GD3 and GD2, respectively. The lymphocytes used for the production of these monoclonal antibodies originate from melanoma patients.

The monoclonal antibodies described in the literature were obtained either from melanoma patients with or without immunisation or by and after immunisation of laboratory animals. However, such efforts for obtaining antibodies which are also effective against melanoma in vivo display great disadvantages. Murine monoclonal antibodies suffer from the disadvantage that they are recognised by the human immune system as foreign proteins and, therefore, antibodies are formed against these foreign proteins. This means that such monoclonal antibodies are eliminated more quickly and thus are limited in their effectiveness. However, also in the case of antibodies which have been obtained from tumour patients, there is great doubt about their effectiveness since, precisely in the case of tumour patients, the functionability of the immune system is impaired. Furthermore, the antibodies of the prior art recognise by no means all primary melanomas and only a small part of melanoma metastases.

Therefore, it is an object of the present invention to provide antibodies against melanoma in the case of which the disadvantages of the prior art are at least partially overcome.

Thus, according to the present invention, there is provided an antibody against melanoma, which is characterised in that it binds to the gangliosides GM3 and GD3 but essentially not to the gangliosides GM1, GM2, GD1a, GD1b and GD2, the binding of the antibody to the gangliosides having been determined by immune staining after thin layer chromatographic separation of the gangliosides.

The antibodies according to the present invention, which are human antibodies, can be obtained by a process in which, without previous immunisation, B-lymphocytes are isolated from healthy subjects, the isolated B-lymphocytes are immortalised, antibodies from the immortalised B-lymphocytes are screened by immuno-histochemical analysis for binding against primary melanoma and/or melanoma metastases, the positively-reacting clones are selected and cultured and monoclonal antibodies are obtained therefrom.

The obtaining of antibodies directed against melanoma from healthy subjects which do not suffer from melanoma is completely surprising. As donor for the B-lymphocytes, there is preferably chosen a healthy person at risk of melanoma. By a person at risk of melanoma is to be understood, for example, a human with a risk of sunburn, i.e. a fair-haired or fair-skinned human, possibly with freckles, who has previously been exposed to an intensive ultra-violet radiation, especially preferably over a comparatively long period of time. The suitability of the process according to the present invention for obtaining human antibodies which are directed against and are also effective against melanoma can possibly be attributed to the fact that apparently in every person cells continuously degenerate, thereby arising melanoma cells which can, however, be successfully combated by the body's own immune system.

The first step of the process according to the present invention is to obtain B-lymphocytes from the blood of a healthy person. A "healthy person" in the meaning of the present invention is defined as a person who displays no symptoms of a melanoma. Obtaining of B-lymphocytes can be carried out by known methods. Subsequently, there follows the immortalisation of the lymphocytes, various methods being available for this purpose. The B-lymphocytes can be fusioned with myeloma cells of human or murine origin according to the method of Köhler and Milstein (Nature, 256,495/1975). However, heteromyelomas can also be used for the fusion. In the same way, it is also possible to transform the B-lymphocytes by means of Epstein-Barr virus. Furthermore, there can be used the processes described in EP-A-0,093,436 or in EP-A-0,256, 512. Fusion is thereby carried out with subcellular vesicles which contain a transforming DNA.

From the immortalised B-lymphocytes, those are selected which produce antibodies with the desired reactivity against melanoma. The selection of the B-lymphocytes for secretion of antibodies which are directed against melanoma and are also effective against metastases is carried out, according to the present invention, by immune-histochemical analysis for binding against melanoma tissue sections, in which case primary melanoma and/or melanoma metastases can be used. The immune-histochemical analysis of the antibodies is preferably done by binding to melanoma in tissue sections by means of an ELISA test with reference to the method of Nielsen et al. (Hybridoma, 6, 103–109/1987). In this way, positively determined B-lymphocytes are selected, cultured according to conventional processes and monoclonal antibodies obtained therefrom according to known methods.

By means of the process according to the present invention, it is possible to obtain antibodies against melanoma which also possess a very high reactivity against melanoma metastases. Thus, the present invention also concerns human antibodies against melanoma which, in tissue sections, also bind at least 70% of the melanoma metastases.

An antibody according to the present invention is characterised in that it binds to the gangliosides GM3 and GD3 but essentially not to the gangliosides GM1, GM2, GD1a, GD1b and GD2. This means that the antibodies according to the present invention bind to the gangliosides GM1, GM2, GD1a, GD1b and GD2 with an affinity of at most about 5% with reference to the affinity for the ganglioside GM3 or the ganglioside GD3. The determination of the binding ability of the antibody according to the present invention to the gangliosides is carried out by immune staining after thin layer chromatographic separation of the gangliosides. By means of this process, it is possible, to decide with reliability whether a specific ganglioside binds to an antibody or not. Less preferred is the determination of the affinity of an antibody according to the method of the ELISA test. In the case of this method, non-specific binding cannot be excluded so that the possibility of falsely positive results exists. These falsely positive results would be manifested by a smaller binding affinity to gangliosides in the case of which, according to the above-described process, no binding is to be ascertained.

Examples of antibodies which can be obtained by the process according to the present invention are the monoclonal antibodies "17" and AH18, secreted by the hybridoma cell lines ECACC 90090703 and ECACC 90090701. These antibodies are of the class IgM. These cell lines have been deposited on Sep. 7, 1990 in compliance with the Budapest Treaty at the European Collection of Animal Cell Cultures (ECACC), Porton Down, Salisbury, Wiltonshire, England.

The present invention also provides human monoclonal antibodies capable of binding in an equivalent manner to the monoclonal antibodies obtainable from the hybridoma cell lines ECACC 90090703 or ECACC 90090701. which have been deposited at the European Collection of Animal Cell Cultures (ECACC) under the provisions of the Budapest Treaty at Porton Down, Salisbury, Wiltshire, England. By the term "antibodies capable of binding in an equivalent manner" are to be understood antibodies in the case of which an epitope overlapping is detectable with the antibodies in question. The epitope overlapping can be detected by a competitive test system. For this purpose, for example with the help of an enzyme immunoassay, there is examined the extent to which an antibody competes with the known antibody for the binding to a defined antigen or special epitope. For this purpose, an appropriately immobilised antigen is incubated with the antibody according to the present invention in labelled form and an excess of the antibody in question. By detection of the bound labelling, there can then easily be ascertained the extent to which the antibody in question can displace the defined antibody from the binding. If there is a displacement of at least 50% in the case of $10^5$ fold excess, then an epitope overlapping is present.

Surprisingly, we have also ascertained that antibodies according to the present invention bind not only to melanoma but also to other tumour tissues, especially lung and mammary carcinoma tissue. An example therefor is the antibody "17" according to the present invention.

The present invention also provides derivatives of antibodies according to the present invention which possess the same binding specifity but with modifications in the region which is not important for the antigen binding. These antibody derivatives can be obtained from antibodies according to the present invention by the exchange of one or more constant domains and/or linkages with another molecule. Thus, for example, an exchange of constant domains for an isotype switch can be carried out where, for example, an antibody of class IgM can be converted into an antibody of class IgG with maintenance of its antigen specificity. This isotype switch can be carried out by cell-biological or molecular-biological methods, which are well known (see, for example, P. Rothman et al., Mol. Cell. Biol., 10, 1672–1679/1990). However, the monoclonal antibodies according to the present invention can also be linked with another molecule, especially a label or a toxin, by means of which its diagnostic or therapeutic usability is changed.

Appropriate processes for the linkage of labels, for example enzymes, such as peroxidase, or of toxins, for example ricin or cholera toxin, with the antibody or radio-active labelling are well known.

The present invention is also concerned with the use of an antibody according to the present invention for the diagnosis or therapy of melanoma and especially for the passive and active immunisation of melanoma patients. It is thereby preferred to use the antibody "17" secreted by the cell line ECACC 90090703 and/or the antibody AH18 secreted by the cell line ECACC 90090701.

Since the monoclonal antibodies obtained by the process according to the present invention bind to living melanoma cells and to other tumour cells, they can be used for combating these cells in the organism. Thus, the present invention also provides a pharmaceutical composition which comprises one or more antibodies according to the present invention, optionally together with conventional pharmaceutical carrier, adjuvant, filling and additive materials. The administration of a medicament according to the present invention is possible not only for prevention of a tumour but also after the metastasing of a tumour and especially of a melanoma. A suitable dosage of the antibody according to the present invention for passive immunisation is in the range of from 1 to 200 mg, whereby this dosage is possibly to be repeatedly administered. The monoclonal antibodies can be administered locally into the melanoma, as described by Irie and Morton (Proc. Natl. Acad. Sci. USA, 83, 8694–8698/1986). However, after metastasing of the melanoma, a systemic administration, such as is conventional, is preferred. The antibodies according to the present invention are preferably used therapeutically alone but can also be used as conjugates with toxins, therapeutics and the like.

Since the antibodies obtained by the process according to the present invention are capable of binding melanomas and melanoma metastases, they are also outstandingly suitable for the qualitative or quantitative detection of melanoma and other tumour cells. The detection thereby takes place in known manner by means of an immunological process of determination. Processes of this type are well known and do not need to be further explained here. The antibodies obtained according to the present invention can thereby be used as unlabelled, labelled and/or immobilised receptor.

The antigens or epitopes defined by means of the monoclonal antibodies can also be detected in body fluids by immunological processes of determination. The monoclonal antibodies according to the present invention can thereby be used as labelled and/or immobilised receptor. Many variants are known for carrying out the process of determination, all of which are suitable. Thus, for example, two, three or more receptors can be used and the incubation with the individual receptors can take place in various sequences in homogeneous or heterogeneous phase. In each case, there is evaluated the signal change due to binding of at least two receptors with the substance to be detected in the sample solution. The determination according to the present invention takes place either in homogeneous phase; for example according to the principle of the agglutination test, in the case of which, as receptors, there are used coated particles, for example latex particles or erythrocytes, which cross-link due to binding with receptors of specific binding capacity and the cells to be detected and thereby agglutinate, or in heterogeneous phase, preferably as a sandwich immunoassay. In every case, at least two receptors $R_1$ and $R_2$ are used of which one contains a monoclonal antibody according to the present invention, for example "17", or an antibody capable of binding in an equivalent manner or a derivative thereof, whereas the other receptor contains another antibody according to the present invention, for example AH18, or an antibody capable of binding in equivalent manner or a derivative thereof.

In the case of incubation of the body fluid with the two receptors, there are formed complexes of $R_1$, ganglioside and $R_2$. The receptors are chosen in such a way that only complexes in which not only $R_1$ but also $R_2$ are bound with the ganglioside give a signal change so that, in this way, only those gangliosides are detected which are capable of binding with both specific antibodies.

The determination according to the present invention preferably takes place as a sandwich immunoassay. For this purpose, receptor $R_1$ is immobilised or made immobilisable and reacted with the sample solution. Subsequently, receptor $R_2$ is added thereto. Complexes are formed of the immobilised receptor $R_1$, the ganglioside to be detected and receptor $R_2$.

The antibodies according to the present invention can also be used for the determination of a prognostic index. After treatment of a melanoma patient, it is thereby ascertained whether the antigen in the body fluids recognised by the monoclonal antibodies, especially in the serum of the patient, appears or disappears after a certain period of time.

Finally, the present invention also provides a process for the diagnosis or therapy of tumours and especially of melanomas, wherein there is administered one or a mixture of several antibodies according to the present invention, optionally together with conventional pharmaceutical carrier, adjuvant, filling and additive materials, preferably in a dosage of from 1 to 200 mg.

The cell lines ECACC 90090703 and ECACC 90090701 mentioned in the present invention, which secrete the antibodies "17" and AH18, were deposited on the 7th Sep., 1990, at the European Collection of Animal Cell Cultures (ECACC), Porton Down, England.

The following Examples are given for the purpose of illustrating the present invention:

EXAMPLE 1

Selection for Antibodies Against Melanoma

From healthy persons 20 to 200 ml of blood were removed and the mononuclear cells isolated therefrom. Subsequently, these cells were immortalised according to conventional methods (Köhler-Milstein or EBV transformation or DNA transfection). After 2 to 4 weeks, the culture supernatants of the immortalised cells were tested. For this purpose, there was carried out an ELISA test on human tissue sections of melanoma. This took place with reference to the method of Nielsen et al., (Hybridoma, 6, 103–109/1987).

Frozen tumour tissues were cut into discs of 3 to 5 μm thickness and applied with silane to glass cover plates. The tissue sections can be stored at −80° C. or can also be used immediately. For this purpose, they were, as required, fixed for 10 minutes at −20° C. in acetone. Subsequently, the acetone was allowed to evaporate if still present and thereafter the sections were dipped for about 3 minutes into PBS (phosphate-buffered saline according to Dulbecco and Vogt, J. Exp. Med., 99,167–182/1954). After the PBS had dripped off, 20 to 30 μl of a blocking antibody (concentration 40 μg/ml) were applied thereto. This blocking antibody was a Fab fragment of a polyclonal sheep serum or of a murine monoclonal antibody against human Fcμ or Fcγ. The blocking antibody was incubated on the sections for 1 to 2 hours or overnight at ambient temperature or at 4° C.

Subsequently, the section was washed three times for about 4 minutes at 4° C. with PBS. The antibody-containing solution, i.e. the culture supernatants of the immortalised cells, was then pipetted thereon. After incubation for several hours (usually for 2 hours) at 4° C., the antibody-containing solution was rinsed away by washing three times for about 4 minutes in PBS. Subsequently, the section was incubated with the same antibody as in the case of the blocking except that this time the monoclonal or polyclonal antibody used was coupled to peroxidase (2 U/ml). Incubation was carried out for 1 hour at 4° C. with subsequent washing as described above. The microscope slides were then dipped into substrate solution (aminoethylcarbazole in dimethyl sulphoxide/tris HCl 50 mmol/l, pH 7.3) in the presence of hydrogen peroxide and incubated for about 4 to 5 minutes. The microscope slides were subsequently washed for about 5 minutes in PBS.

If desired, the cell nuclei in the tissue sections can be stained with Haemalaun (Merck, diluted 1:3 with water). For this purpose, the microscope slides were dipped for about 20 seconds in the Haemalaun solution and subsequently "blued" in two PBS baths, in each case for about 5 minutes.

For storage, the sections were subsequently coated with an aqueous embedding agent, for example glycerol-gelatine (Merck) or Krystal Mount (Biomeda Corp., Foster City, Calif.).

Cell lines which produced the desired antibodies were expanded and cloned. The clones obtained were also analysed as described above. The clones which produced the desired antibodies were further cultured and the antibodies produced by these clones were obtained according to known methods.

By means of this process, there could be obtained the antibodies "17" and AH18 according to the present invention.

EXAMPLE 2

Antibody Specificity Test

In order to determine the specificity of the human monoclonal antibodies obtained according to Example 1 from the immortalised cell lines, a test was carried out for the binding to human primary melanoma and to human melanoma metastases. The test was carried out in the manner described in Example 1. With the antibodies "17" and AH18 according to the present invention, the following results were thereby obtained:

TABLE 1

| human monoclonal antibody | Nävi | reactivity with | |
|---|---|---|---|
| | | primary melanoma | metastases |
| | | (number positive/number tested) | |
| "17" | 28/29 | 48/52 (90%) | 54/54 (100%) |
| AH18 | 23/26 | 48/54 (90%) | 43/51 (80%) |

EXAMPLE 3

3.1. Binding Capacity of the Antibody to Normal Tissue

The monoclonal antibody "17" obtained according to Example 1 was tested for its binding capacity with normal tissue. The test was carried out as described in Example 1.

The antibody was tested for reactivity against human tissue from the brain (cortex, pons, thalamus, corpus amygdaloideum), retina, skin (keratinocytes, melanocytes, Langerhans' cells, endothelial cells, smooth musculature, sweat glands, nerve fibres), muscle, mammary glands, uterus, urinary bladder, gall bladder, spleen, kidney, adrenals, lungs, parotid gland, intestine, erythrocytes (4 commercial test samples and 300 blood donors) and parathyroid. No reaction was found of the antibody according to the present invention with the above types of tissue.

3.2. Binding Capacity of the Antibody to Tumours

In order to determine the further specificity of the human monoclonal antibodies obtained from the immortalised cell lines, further tests were carried out on human tumour tissues. The test was carried out as described in Example 1. With the antibodies according to the present invention, the following results were thereby obtained:

TABLE 2

| tumour | reactivity with "17" and AH18 number positive/number tested |
| --- | --- |
| melanoma | 48/52 |
| lung carcinoma | 10/19 |
| mammary carcinoma | 4/9 |

EXAMPLE 4

Furthermore, the reactivity of the monoclonal antibodies against purified gangliosides was investigated in an immunoblot after thin layer chromatography of the gangliosides.

For this purpose, there were used the gangliosides GM3, GM2 and GD1a of Boehringer Mannheim GmbH, GD2 and GD3 of Biocarb, Sweden, GM1 of Fidia, Italy and GD1b of Pallmann, München. Thin layer plates HPTLC Alu silica gel 60 $F_{254}$ were obtained from Merck. The HPTLC plate was developed with chloroform:methanol:water (0.02% calcium chloride dihydrate) 60:40:0 v/v/v. As fixing agent for the thin layer plates, there was used high molecular weight polyisobutyl acrylate (Aldrich Chemicals) in the form of a 0.1% solution in hexane.

Carrying Out

The procedure and modifications thereof are well known and are here given only by way of example.

Sample Application

5 µl of a 1 mg/ml solution of the gangliosides were applied, the above-mentioned developing agent being used as solvent. The samples were applied successively, for example with a Hamilton syringe, in an about 5 mm wide strip on the thin layer plate; inbetween, they were always allowed to dry well in order that the coating remained as thin as possible. Finally, the thin layer plate was again well dried with a hot-air blower. The plate was introduced into a chamber saturated with developing agent and incubated until the developing agent had moistened about 80% of the plate. The plate was subsequently removed and allowed to dry.

The plate was then rinsed in 0.1% polyisobutyl acrylate solution for about 1 minute, whereafter the plate was again allowed to dry. For the purpose of blocking, the plate was covered with a 1% BSA/PBS solution (bovine serum albumin of Boehringer Mannheim GmbH) using a pipette (under avoiding any air bubbles!) and left to stand for about 30 minutes at ambient temperature. Thereafter, the blocking solution was poured off.

Subsequently, washing was carried out twice with PBS. For this purpose, the plate was immersed in PBS in a dish and, in each case, left for 2 minutes. Inbetween, the PBS was sucked off (never apply the PBS directly to the plate; do not shake; do not allow the plate to dry out).

Thereafter, the plate was covered with a solution containing the monoclonal antibody (concentration 1 to 10 µg/ml) and left for 1 hour at ambient temperature.

Subsequently, it was washed five times with PBS (as described above). The plate was then covered with conjugate (polyclonal, peroxidase-labelled sheep Fab fragment against human Fcµ, concentration as in the case of the tissue test in Example 1) and incubated for 1 hour at ambient temperature. Subsequently, the plate was washed six times with PBS as described above. The substrate was then added thereto and the plate gently moved during the development.

As substrate, there was used TMB/DONS (tetramethylbenzidine (TMB) 12 mg +dioctyl sodium sulphosuccinate (DONS) 40 mg dissolved in 10 ml methanol and mixed with 10 ml citric acid/phosphate buffer, pH 5.0 (25 ml 0.1M citric acid, Merck, +28 ml 0.2M disodium monohydrogen phosphate dihydrate, Merck, to 100 ml), as well as with 10 µl 30% hydrogen peroxide. It was developed as long as the negative control was not stained and then washed several times with distilled water. The plate was dried while protecting from light and immediately photographed since the staining with TMB/DONS bleaches.

If the above-described procedure is carried out with MAB "17" or with MAB AH18, then there are obtained the results shown in the following Table 3. The MAB's "17" and AH18 react with GM3 and GD3 but not with GM1, GM2, GD1a, GD1b and GD2.

For control, the gangliosides were made visible in a parallel experiment by staining with resorcinol. For this purpose, the plate was sprayed with resorcinol solution (resorcinol from Merck, 400 ml +100 ml water +5 ml sulphuric acid) and developed for about 10 minutes in a drying cabinet at 110° C. This control shows that, of all gangliosides, equal amounts had been applied to the thin layer plate.

TABLE 3

Detection of gangliosides by thin layer chromatography

| ganglioside | resorcinol | MAB "17" or MAB AH18 |
| --- | --- | --- |
| GM1 | + | − |
| GM2 | + | − |
| GM3 | + | + |
| GD1a | + | − |
| GD1b | + | − |
| GD2 | + | − |
| GD3 | + | + |

From Table 3, it can be seen that the antibodies according to the present invention only react with certain gangliosides. Of the tested gangliosides, GM3 and GD3 show positive signals. No noteworthy reactivity (<5%) was found with gangliosides GM1, GM2, GD1a, GD2 and GD1b.

EXAMPLE 5

Reactivity of the Antibodies with Cell Lines

Cells of the cell lines to be investigated were cultured overnight in Terasaki plates (obtained from the firm Greiner). The culture supernatant was removed from the adherent cells and replaced by the antibody solution to be investigated. After incubation for 1 to 2 hours, the antibody solution was removed, the cell "lawn" washed several times and the monoclonal antibodies bound to the cells were detected. For this purpose, after washing with PBS, 100 µl peroxidase-labelled sheep anti-human light chain antibody were added thereto and again incubated at ambient temperature for 1 to 2 hours. After renewed washing, the enzyme reaction was started with a peroxidase substrate (ABTS®). After 10 to 60 minutes at ambient temperature, the extinction was determined in a photometer at 406 nm. Alternatively thereto, there can also be added a peroxidase substrate, such as aminoethylcarbazole, and, after ending of the reaction, the brownish precipitate in or on the cells evaluated by means of a microscope.

From the results shown in the following Table 4, it follows that the antibody "17" reacts with melanoma SK-MEL 28 cells (ATCC HTB 72), whereas no reaction was found with human prepuce fibroblasts (which were themselves isolated by known processes). Furthermore, the antibody "17" showed reaction with insulinoma cell RIN (obtained from Dr. Eisenbart, Josslin Diabetes Center, Boston, Mass. 02215) and the neuroblastoma cells IMR 32 (ATCC CCL 127).

TABLE 4

Antibody reactivity against various cells

| antibody | SK MEL 28 (melanoma) | RIN (insulinoma) | IMR32 (neuro-blastoma) | human prepuce fibroblasts |
| --- | --- | --- | --- | --- |
| "17" | ++ | + | + | − |

EXAMPLE 6

Determination of Epitope Overlapping of Antibodies Against Melanoma

For the detection of the epitope overlapping of an antibody with one of the monoclonal antibodies ECACC 90090703 or ECACC 90090701, there was carried out a competitive enzyme immunoassay. For this purpose, the gangliosides GM3, GM2, GD1a, GD2, GD3, GM1 and GD1b (obtained from Boehringer Mannheim GmbH, Biocarb, Pallmann or Fidia; cf. Example 4) were dissolved in methanol (10 µg/ml) and, in each case, 100 µl of this solution were pipetted into 96-well microtitre plates (Greiner). After evaporation of the solution (either overnight at ambient temperature or for 1 hour at 37° C.), washing was carried out with PBS and then non-specific binding positions were blocked with a 1% crotein C solution in PBS (incubation at ambient temperature for 1 to 2 hours and washing with PBS/0.05% Tween 20). Subsequently, incubation was carried out for 90 minutes at ambient temperature simultaneously with one of the monoclonal antibodies ECACC 90090703 or ECACC 90090701 which had been labelled with peroxidase (end concentration 250 mU/ml) and with the antibody to be assessed. After washing again four times with PBS/0.05% Tween 20, incubation was carried out for 30 minutes with buffer containing the enzyme peroxidase substrate ABTS® in sodium perborate at ambient temperature and subsequently the extinction was measured at 405 nm as a measure for the amount of the bound, peroxidase-labelled monoclonal antibody ECACC 90090703 or ECACC 90090701. This value is compared with the extinction which was obtained in the case of incubation with the monoclonal antibody ECACC 90090703 or ECACC 90090701 alone (with the addition of a corresponding amount of buffer for the compensation of the dilution effect arising in the case of the addition of the antibody to be assessed). When, with up to a $10^5$ fold excess of antibody to be assessed with regard to the monoclonal antibody ECACC 90090703 or ECACC 90090701 enzyme conjugate (250 mU/ml), at least 50% competition is to be recognised, then an epitope overlapping is present.

We claim:

1. Human monoclonal antibody 17, produced by the hybridoma cell line ECACC 900900703, and antibody derivatives thereof, which binds the gangliosides GM3 and GD3, and does not bind the gangliosides GM1, GM2, GD1a, GD1b and GD2 in an amount greater than about 5% of the extent to which said antibody binds to gangliosides GM3 and GD3 as determined by immune staining after thin layer chromatographic separation of the gangliosides, said antibody 17 recognizes an antigen on a melanoma which expresses at least gangliosides GM3 and GD3.

2. Human monoclonal antibody AH18, produced by the hybridoma cell line ECACC 900900701, and antibody derivatives thereof, which binds the gangliosides GM3 and GD3, and does not bind the gangliosides GM1, GM2, GD1a, GD1b and GD2 in an amount greater than about 5% of the extent to which said antibody binds to gangliosides GM3 and GD3 as determined by immune staining after thin layer chromatographic separation of the gangliosides, said antibody AH18 recognizes an antigen on a melanoma which expresses at least gangliosides GM3 and GD3.

3. A human monoclonal antibody or derivative thereof which binds the same epitope as the antibody of claim 1.

4. A human monoclonal antibody or derivative thereof which binds the same epitope as the antibody of claim 2.

5. An antibody according to claim 1 or 2, wherein said antibody is an IgM antibody.

6. The human monoclonal antibody of claim 1 which binds an antigen which expresses at least gangliosides GM3 and GD3 found on lung carcinoma and mammary carcinoma.

7. A derivative of an antibody according to any one of claims 1–4, wherein said antibody is linked with another molecule, comprising at least one member selected from the group consisting of labels and toxins.

8. A human monoclonal antibody of any one of claims 1–4 which is effective in the in vitro diagnosis of a melanoma which has an antigen which expresses at least gangliosides GM3 and GD3.

* * * * *